United States Patent [19]

Willay et al.

[11] Patent Number: 4,732,478

[45] Date of Patent: Mar. 22, 1988

[54] PROCESS FOR DETERMINING, BY OPTICAL EMISSION SPECTROMETRY, THE CONTENT IN A STEEL OF AN ELEMENT SUCH AS ALUMINUM, IN THE DISSOLVED STATE AND IN THE PRECIPITATED STATE

[75] Inventors: Gérard Willay, Ars-sur-Moselle; Bernard Boury; André Wittmann, both of Metz, all of France

[73] Assignee: Institut de Recherches de la Siderurgie Francaise, Maizieres-Les-Metz, France

[21] Appl. No.: 853,757

[22] Filed: Apr. 18, 1986

[30] Foreign Application Priority Data

Apr. 25, 1985 [FR] France .................... 85 06363

[51] Int. Cl.⁴ .................................... G01N 21/67
[52] U.S. Cl. ........................................ 356/313
[58] Field of Search ................ 356/303, 307, 313

[56] References Cited

U.S. PATENT DOCUMENTS 4,111,556 9/1978 Grisar et al. .................... 356/313
4,326,801 4/1982 Ono et al. ....................... 356/313

FOREIGN PATENT DOCUMENTS 0054012 10/1981 European Pat. Off. .
0101364 2/1984 European Pat. Off. .
0110834 6/1984 European Pat. Off. .
0125171 11/1984 European Pat. Off. .
2139347 11/1984 United Kingdom .

OTHER PUBLICATIONS

Rapport De Recherche, completed 1-21-86 by Examiner Callewaert-Haezebrouck at Institut National de la Propriete Industrille.

*Primary Examiner*—Vincent P. McGraw
*Attorney, Agent, or Firm*—Staas & Halsey

[57] ABSTRACT

A sample of the steel to be analyzed is subjected to spark discharging, the optical emission of the sparks is directed onto a diffraction grating in order to separate the light emission corresponding to the element to be metered and a capacitor is charged by a current respective of the intensity of this radiation; after every elementary discharge of the integration circuit, the charge of the capacity is converted into the form of a digital data representative of the intensity of the line selected; during a spark discharging cycle, the number of intensities is determined of which the value is included in each one of a plurality of contiguous channels, in order to set up an intensity frequency diagram as a function of the intensity; the curve representing the diagram is smoothed and the content of dissolved element is determined as a linear function of the value of light intensity corresponding to the peak of the gaussian part of the smoothed curve; and the content of precipitated element is determined by summing products $n_i$, $C_i$ for all the channels located beyond the gaussian part, on the high intensity side, where $n_i$ and $C_i$ are the number of pulses in channel i, and the middle intensity of channel i, respectively.

5 Claims, 4 Drawing Figures

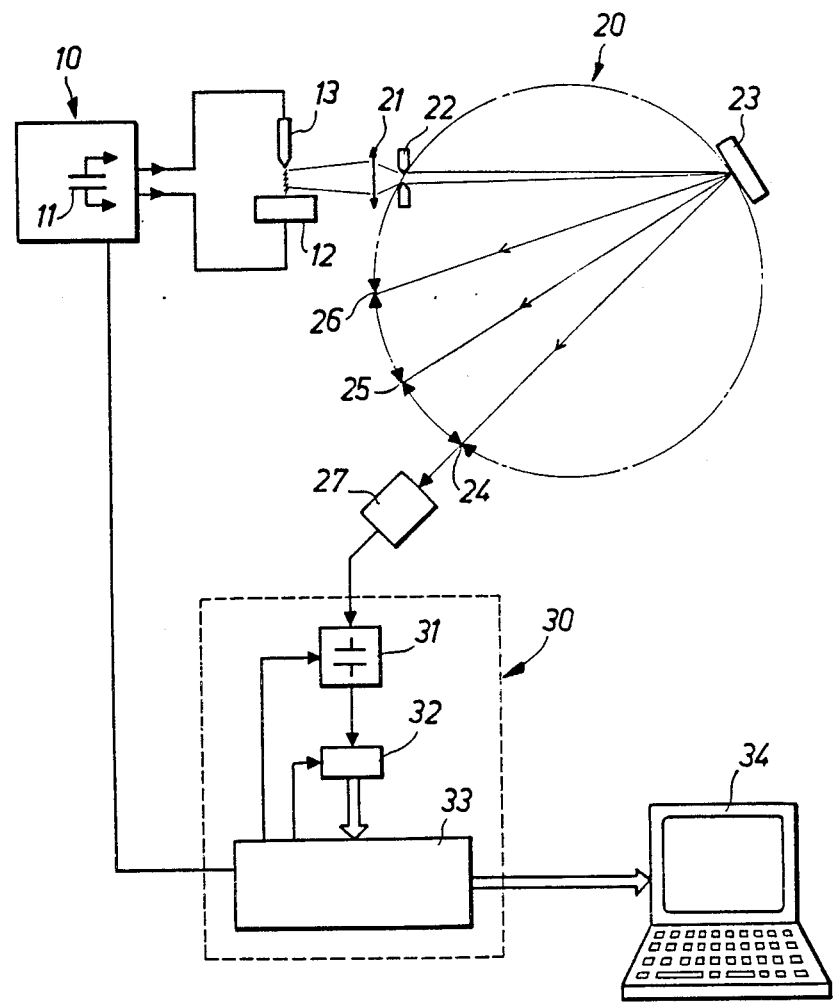
Fig_1

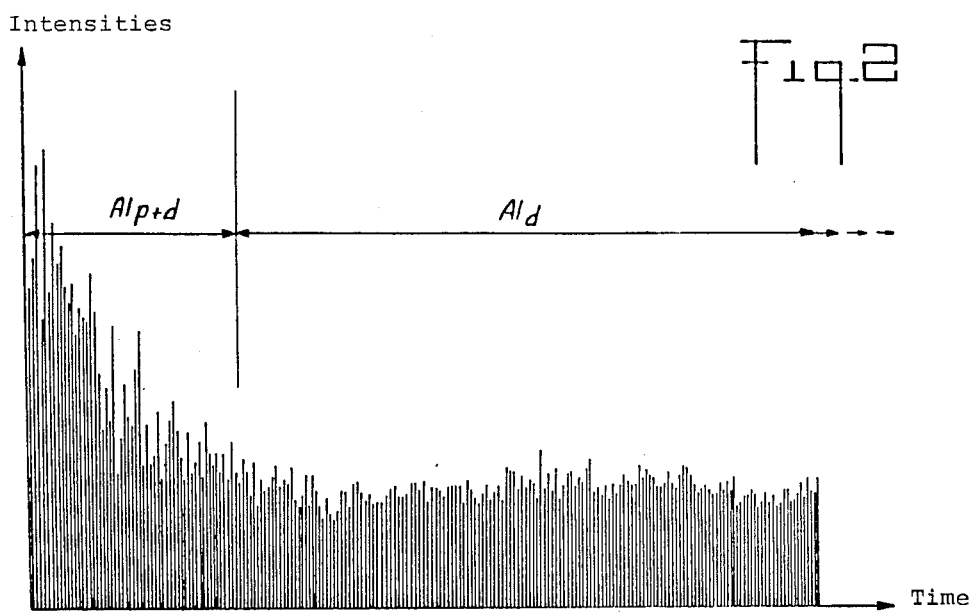
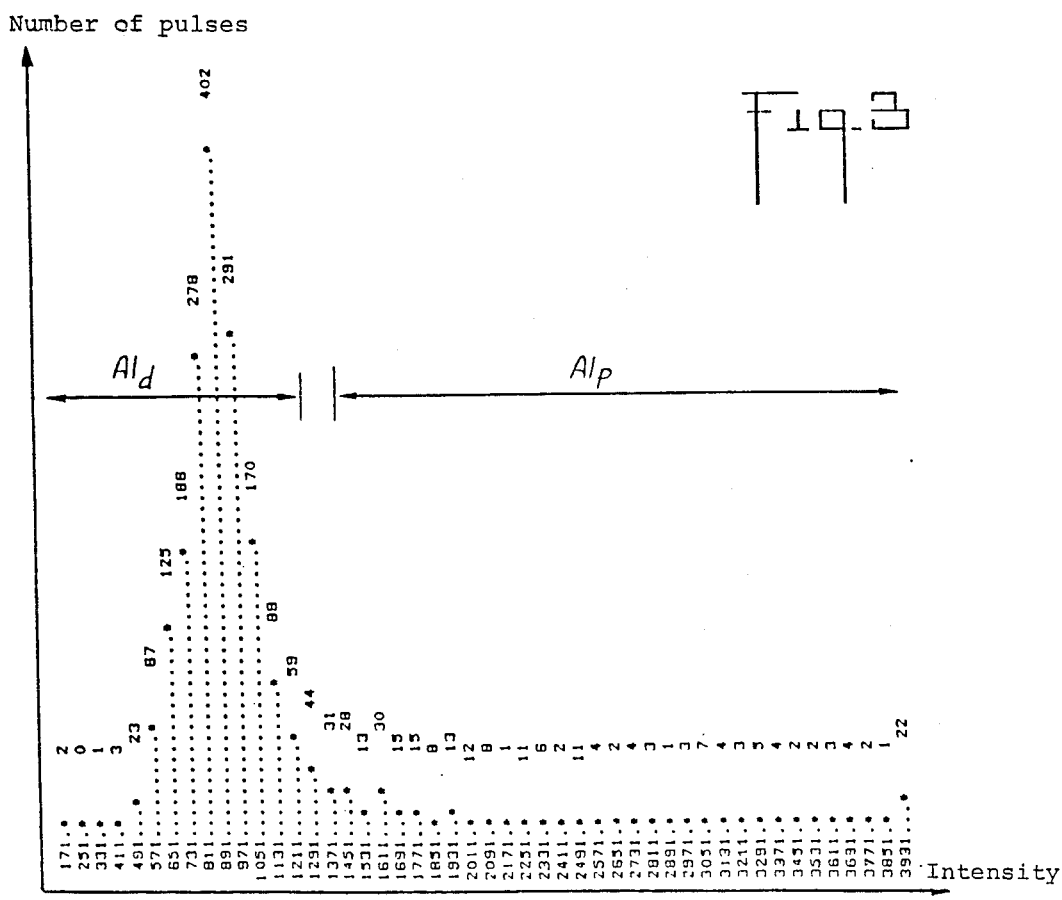

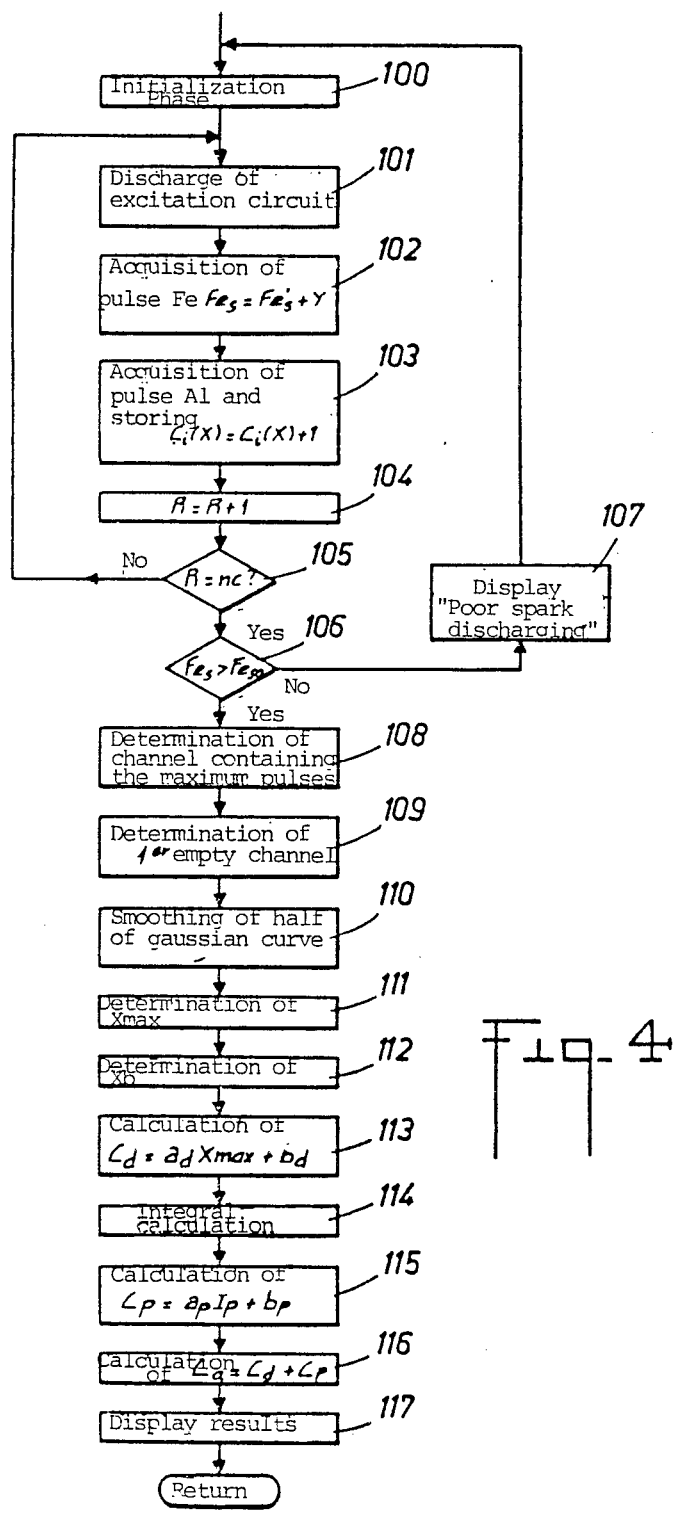

PROCESS FOR DETERMINING, BY OPTICAL EMISSION SPECTROMETRY, THE CONTENT IN A STEEL OF AN ELEMENT SUCH AS ALUMINUM, IN THE DISSOLVED STATE AND IN THE PRECIPITATED STATE

BACKGROUND OF THE INVENTION

The present invention relates to the determination, by optical emission spectrometry, of the content in a steel of an element such as aluminium, in the dissolved state and in the precipitated state.

The large majority of steels made by continuous casting is steel treated with aluminium. In fact, aluminium confers a certain number of mechanical properties on steel, in particular by its aptitude to form nitrides enabling the size of the grain to be monitored. Furthermore, aluminium is a calming agent.

The aluminium present in the steel is, in particular, in oxidized from (precipitated aluminium, or $Al_p$) and in solid solution (dissolved aluminium, or $Al_d$). In order to make steel in optimal manner, it is necessary to know the $Al_p$ content quickly, in order to assess the cleanness of the metal, and the $Al_d$ content in order to know whether the ranges of content envisaged are respected.

Optical emission spectrometry has been currently employed for some years to follow the making of cast iron and steel. Aluminium forms part of the elements metered by this technique.

Optical emission spectrometry consists in subjecting a sample to be analyzed to spark discharging, in directing the optical emission of the arc onto a diffraction grating, and in collecting on a photomultiplier the light beam of the line of which the wave length corresponds to the element to be metered.

According to the method of integration, the current delivered by the photomultiplier is accumulated in a capacitor for a certain time then, when spark discharging is finished, the total charge of the capacitor is measured in order to determine the concentration of the element to be dosed.

It has appeared that the signal delivered by the spectrometer in the course of a spark discharging cycle is formed by components which may be arranged in two groups as a function of their intensities. In fact, if the case of aluminium is considered for example, when, at the point of impact of the spark on the sample, there is an inclusion of precipitated aluminium, the light intensity if much greater than if, at the point of impact, there is only dissolved aluminium. This observation led to imagining the method for so-called sorting (or discrimination) of the pulses. In this latter method, the charge of the integration capacitor is measured, not at the end of a spark discharging cycle, but after each elementary discharge of the excitation circuit and the values measured are stored in order to be subsequently exploited (U.S. Pat. No. 4,326,801).

SUMMARY OF THE INVENTION

It is an object of the present invention to provide a process using the method of sorting the pulses in optical emission spectrometry in order finely to determine the content in a steel of an element such as aluminium, in the dissolved state and in the precipitated state.

This object is attained thanks to a process whereby, according to the invention:

the content in a steel of an element such as aluminium, in the dissolved state and in the precipitated state is determined by optical emission spectrometry, said process comprising the steps of:

subjecting a sample of the steel to be analyzed to spark discharging by causing an excitation circuit to generate sparks by successive elementary discharges;

directing the optical emission of the sparks onto a diffraction grating so as to separate a light emission corresponding to the element to be metered;

charging an integration capacitor with a current representative of the intensity of the light emission in response to each of said elementary discharges;

converting the value of the charge of said capacitor into digital data;

registering said digital data so as to store the various digital data representative of the respective light emission intensities responsive to said successive elementary discharges constituting a spark discharging cycle;

determining among said stored digital data the number of intensities having a value comprised in each of a plurality of contiguous channels in order to set up a frequency diagram as a function of the light emission intensity;

smoothing a curve representative of said frequency diagram, said smooth curve showing a part of substantially gaussian course on the low intensity side;

determining the content of dissolved element as a linear function of the intensity value corresponding to the maximum peak of said gaussian part of the smoothed curve; and determining the content of precipitated element by summing products $n_i$, $c_i$ for all the channels located beyond the gaussian part, on the high intensity side of said frequency diagram, where $n_i$ is the number of intensities in channel i and $c_i$ is the middle intensity value of the same channel i.

DESCRIPTION OF THE DRAWINGS

The invention will be more readily understood on reading the following description with reference to the accompanying drawings, in which:

FIG. 1 is a very schematic view of a device for carrying out the process according to the invention.

FIG. 2 is a buckling profile illustrating the variation in time of the light intensity collected in the course of a spark discharging cycle.

FIG. 3 is a frequency diagram illustrating the distribution of the number of pulses collected as a function of the corresponding light intensity, and FIG. 4 is a flow chart illustrating the operations effected in the course of carrying out the process of the invention by means of a micro-computer programmed to that end.

DESCRIPTION OF A PREFERRED EMBODIMENT

Referring now to the drawings, the device shown in FIG. 1 essentially comprises a spark discharge generator 10, an optical device 20 for detecting the lines corresponding to the elements to be metered and a measuring assembly 30.

Generator 10 is for example of the type described in French Patent Appln. No. 82 13662. It is equipped with a low-capacity capacitor 11 (for example 3 μF). Capacitor 11 is discharged under some hundreds of volts and at a given frequency in order to establish a spark between a sample 12 to be analyzed and a counter-electrode electrode 13 placed at a short distance. Sample 12 is made of steel of which the content of dissolved aluminium and of precipitated aluminium is to be measured. By choosing for example a discharge frequency of 100 Hz and a duration of a spark discharging cycle of 20 s, the cycle is constituted by 2000 elementary discharges of the excitation circuit, i.e. 2000 sparks which succeed one another every 10 ms.

Optical device 20 comprises a convergent lens 21 of which the object focus is on the arc formed between the sample 12 and the electrode 13, and a slot 22 which collects the light emission of the arc and sends a light beam onto a diffraction grating 23. The latter emits a spectrum of lines representative of the constituents of sample 12. Different scanning windows 24, 25, 26 are placed opposite grating 23 on a circle which passes through this grating and the centre of slot 22. Each window receives a radiation of a given wave length. Window 24, for example, is disposed so as to receive the radiation of the line relative to aluminium (wave length equal to 396.1 nm). A photomultiplier tube 27 is placed behind window 24 to deliver a current of which the intensity represents the light intensity of the radiation of the corresponding line.

The current leaving the photomultiplier 27 charges an integrator 31 constituted by a capacitor of the measuring assembly. The integration capacitor 31 is of very low capacity, for example 100 pF.

In accordance with the "pulse-sorting" method, a spark discharging cycle is divided into consecutive elementary sequences each comprising:
 discharge of the excitation circuit (capacitor 11),
 integration in the capacitor 31 for a predetermined duration of integration (for example 0.5 ms),
 acquisition of the intensity of the pulse (charge of integration capacitor 31) at the end of the period of integration, conversion of the amplitude of the pulse into digital form, and memorization,
 return to zero (discharge) of the integration capacitor 31.

Synchronization between the discharge of the excitation circuit and the acquisition of the measurement is effected by controlling these operations by means of signals both derived from the frequency of the A.C. electrical supply network and elaborated by a processing and control unit 33 forming part of measuring assembly 30.

The amplitude of each pulse is converted into digital form by means of an analog-to-digital converter 32 (for example of 12 bits) connected to the integration capacitor 31. At the output of the converter, there is thus a digital signal whose value X is representative of the light intensity translated by the amplitude of the pulse collected.

The histogram corresponding to a spark discharging cycle is registered in an addressable memory 34 in the following manner:

The scale of the intensities measured (i.e. 0 to 4095 for the digital values X in the case of a coding on 12 bits), is divided into contiguous zones or channels of predetermined width. The channels are associated with respective compartments in the addressable memory 34. The measuring unit 30 operates under the control of a micro-processor. When a value X is available at the output of the converter at the end of a period of integration, an acquisition program is triggered off which determines the channel in which is found value X and increments the contents of the corresponding compartment of memory 34.

At the end of the spark discharging cycle, memory 34 therefore contains the pulse frequency diagram, i.e. the distribution of the pulses as a function of the light intensity that they represent.

FIG. 2 shows an example of buckling profile, i.e. the intensities measured in the course of consecutive elementary sequences. The buckling profile therefore corresponds to the variation of time, in the course of the spark discharging cycle, of the signal measured at the terminals of the integration capacitor.

At the beginning of spark discharging, relatively high intensities are observed, due to the impact of the spark on inclusions of precipitated aluminium ($Al_p$) to which is added the participation of the dissolved aluminium ($Al_d$). After a first period of the spark discharging cycle, the intensities measured translate the dissolved aluminium.

FIG. 3 shows the corresponding frequency diagram, as registered in memory 34. In this example, the scale of the intensities measured (0 to 4095) is divided into channels of width equal to 80. As shown in FIG. 2, it is observed that a majority of intensities is found in channels lying on the low intensity side with, in this part of the diagram, a substantially gaussian distribution due to the contribution of $Al_d$. The part of the diagram lying beyond this part of gaussian course, on the high intensity side, has a substantially horizontal course, with an accumulation in the last channel due to the presence of intensities out of scale (upward overshooting of the measuring scale).

In accordance with the invention, the gaussian part of the frequency diagram is smoothed in order to determine the location of the maximum. It has proved that this gaussian part is distributed on the high intensity side by pulses coming from $Al_p$. Calculation for the smoothing of the gaussian curve is therefore made for the first half thereof, on the low intensity side, the other half being deduced by symmetry. The content $C_d$ of $Al_d$ is then calculated not by integration of the gaussian part, but according to a linear function of the Xmax intensity corresponding to the peak of the smoothed gaussian curve:

$$C_d = a_d \cdot X\text{Max} + b_d$$

It has, in fact, been established that the correlation between the Xmax intensity and the content determined by chemical analysis is good. This intensity Xmax is that corresponding to the middle of the channel where the peak of the smoothed curve is found. For determining the content $C_p$ of $Al_p$, it is not possible to proceed in the same manner by reason of the spreading of the number of pulses over the scale of the intensities beyond the gaussian part. One must therefore resort to the technique of integration. However, the cutoff between the pulses coming from $Al_d$ and those coming from $Al_p$ is not sharp. There is a mixed zone which comprises a certain number of steps on the intensity scale. It is preferable not to take these steps into account. If Xb designates the intensity corresponding to the point of return to the base line of the smoothed gaussian curve, the integral $I_p$ is calculated between the channel containing this point (or any channel slightly offset towards the high intensities), and the end of the frequency curve:

$$I_p = \sum_{i=Xb}^{i=N} n_i \cdot C_i$$

where $n_i$ is the frequency (number of pulses) and $C_i$ the intensity for channel i, whilst N is the total number of channels. The concentration $C_p$ is then determined according to a linear function of the integral $I_p$:

$$C_p = a_p \cdot I_p$$

The concentration $C_s$ of total aluminium is simply the sum of concentrations $C_d$ and $C_p$.

The acquisition of the measurements, the processing of the frequency diagram and the calculation of the aluminium contents are effected under the control of a program implanted in unit 33. FIG. 4 is an example of flowchart illustrating the operations relative to the treatment of a sample.

In this example, the total content of iron $Fe_s$ is measured by integration in order to assess the quality of spark discharging. This measurement is effected by means of a measuring chain (not shown in FIG. 1), through the scanning window of which the location corresponds to the line relative to iron.

Before the beginning of acquisition, the contents $C_i$ of the compartments of memory 34 are returned to zero, as well as the parameters k and $Fe_s$ (initialization phase 100).

Acquisition of the measurements comprises, for each spark, control of the discharge of the excitation circuit (phase 101); acquisition of pulse Y corresponding to iron, by running total $Fe_s = Fe_s + Y$ (phase 102); acquisition of the pulse corresponding to aluminium and incrementation of the contents of the compartment of memory 34 corresponding to the channel in which is found the intensity of the collected pulse $C_i(X) = C_i(X) + 1$ (phase 103); incrementation of parameter k (phase 104) and comparison thereof with the preregistered number nc of elementary sequences constituting a spark discharging cycle (test 105). When k=nc, the acquisition phase is finished.

If the cumulated value $Fe_s$ is less than a predetermined threshold value $Fe_{so}$ (test 106), a message "poor spark discharging" is displayed on the screen of a monitor 34 connected to unit 33 (phase 107) before possible return to phase 100.

If the cumulated value $Fe_s$ is correct, the frequency diagram is processed in order firstly to effect smoothing of the part of gaussian course. To that end, the channel containing the largest number of pulses is firstly determined (phase 108) then, starting from this channel, and in the direction of the low intensities, the first channel not containing pulses is sought (phase 109). Smoothing of the left-hand part of the gaussian curve is then effected (phase 110); any method of curve smoothing known per se may be used (for example the so-called least error squares method).

After smoothing, the abscissa Xmax of the maximum of the gaussian curve is determined by seeking the point of zero derivative (phase 111), as well as the abscissa Xb of the point of return of the curve to the base line, on the high intensity side (phase 112).

The content $C_d$ of $Al_d$ is calculated by:

$$C_d = a_d \cdot X_{max} + b_d \text{(phase 113)}.$$

The part of the diagram lying beyond the gaussian part on the high intensity side (i.e. beyond Xb) is integrated in order to furnish the integral $I_p$ (phase 114) and the content $C_p$ of $Al_p$ is calculated by:

$$C_p = a_p \cdot I_p \text{(phase 115)}.$$

The coefficients $a_d$, $a_p$ and the values $b_d$, $b_p$ are predetermined by calibration.

The content $C_s$ of total aluminium may then be calculated by $C_s = C_d + C_p$ (phase 116) and the results are displayed on the screen of the monitor 34 (phase 117) whilst awaiting a possible new cycle.

What is claimed is:

1. A process for determining, by optical emission spectrometry, the content in a steel of an element such as aluminium, in the dissolved state and in the precipitated state, said process comprising the steps of:
    subjecting a sample of the steel to be analyzed to spark discharging by causing an excitation circuit to generate sparks by successive elementary discharges;
    directing the optical emission of the sparks onto a diffraction grating so as to separate a light emission corresponding to the element to be metered;
    charging an integration capacitor with a current representative of the intensity of the light emission in response to each of said elementary discharges;
    converting the value of the charge of said capacitor to digital data;
    registering said digital data so as to store the various digital data representative of the respective light emission intensities responsive to said successive elementary discharges constituting a spark discharging cycle;
    determining among said stored digital data the number of intensities having a value comprised in each of a plurality of contiguous channels in order to set up a frequency diagram as a function of the light emission intensity;
    smoothing a curve representative of said frequency diagram, said smooth curve showing a part of substantially gaussian course on the low intensity side;
    determining the content of dissolved element as a linear function of the intensity value corresponding to the maximum peak of said gaussian part of the smooth curve; and
    determining the content of precipitated element by summing products $n_i$, $C_i$ for all the channels located beyond the gaussian part, on the high intensity side of said frequency diagram, where $n_i$ is the number of intensities in channel i and $C_i$ is the middle intensity value of the same channel i.

2. The process of claim 1, wherein said gaussian part of the curve is smoothed only on the half thereof lying on the low intensity side.

3. The process of claim 1, wherein said summing of products $n_i$, $C_i$ is performed for all the channels located beyond the point of return of the smoothed gaussian part of the curve to the base line, on the high intensity side.

4. The process of claim 1, wherein said spark discharging and said digital data registration are controlled by means of signals derived from an AC electrical supply network.

5. The process of claim 1, wherein the content of the precipitated element is determined as a linear function of the sum obtained by summing said products $n_i$, $C_i$.

* * * * *